(12) United States Patent
Myers (10) Patent No.: US 6,964,742 B2
(45) Date of Patent: Nov. 15, 2005

(54) METHOD FOR REDUCING MALODORS IN HYDROTROPIC COMPOSITIONS

(75) Inventor: E. Gary Myers, Scottsdale, AZ (US)

(73) Assignee: The Dial Corporation, Scottsdale, AZ (US)

(*) Notice: Subject to any disclaimer, the term of this patent is extended or adjusted under 35 U.S.C. 154(b) by 352 days.

(21) Appl. No.: 10/138,140

(22) Filed: May 1, 2002

(65) Prior Publication Data

US 2003/0008800 A1 Jan. 9, 2003

Related U.S. Application Data

(60) Provisional application No. 60/287,765, filed on May 1, 2001.

(51) Int. Cl.[7] .............................................. B01D 15/00
(52) U.S. Cl. ...................................................... 210/690
(58) Field of Search ................................. 210/670, 674, 210/690, 666

(56) References Cited

U.S. PATENT DOCUMENTS

| | | |
|---|---|---|
| 3,689,404 A | 9/1972 | Carpenter et al. |
| 3,763,070 A | 10/1973 | Timpe et al. |
| 3,970,605 A | 7/1976 | Wentworth |
| 3,996,161 A | 12/1976 | Chia |
| 4,043,904 A | 8/1977 | Takeda et al. |
| 4,072,479 A | 2/1978 | Sinha et al. |
| 4,138,506 A | 2/1979 | Eida et al. |
| 4,252,643 A | 2/1981 | Kenttig et al. |
| 4,518,504 A | 5/1985 | Wolcott |
| 4,544,488 A | 10/1985 | O'Brien |
| 4,661,259 A | 4/1987 | Walterick, Jr. et al. |
| 4,668,403 A | 5/1987 | Walterick, Jr. et al. |
| 4,737,293 A | 4/1988 | Walterick, Jr. et al. |
| 4,985,150 A | 1/1991 | Cronje et al. |
| 5,021,164 A | 6/1991 | Gay |
| 5,310,568 A | 5/1994 | Lini |
| 5,368,738 A | 11/1994 | Dussert et al. |
| 5,368,739 A | 11/1994 | Dussert et al. |
| 5,466,378 A | 11/1995 | Dussert et al. |
| 5,904,854 A | 5/1999 | Shmidt et al. |
| 6,056,876 A | 5/2000 | Yamasaki et al. |
| 6,107,261 A | 8/2000 | Taylor et al. |
| 6,136,771 A | 10/2000 | Taylor et al. |
| 6,670,317 B2 * | 12/2003 | Severns et al. ............. 510/285 |

FOREIGN PATENT DOCUMENTS

| | | |
|---|---|---|
| EP | 370-397 A | 5/1990 |
| GB | 262.131 | 5/1927 |
| GB | 702.955 | 1/1954 |
| GB | 1408885 | 10/1975 |
| JP | J5-2073-838 | 6/1977 |
| JP | J5-3016-464 | 2/1978 |
| WO | WO 9606152 | 2/1996 |

OTHER PUBLICATIONS

International Search Report dated Jul. 23, 2002; PCT/US/02/13964, International Filing Date: Jan. 5, 2002, file reference 29930.8216; 4 pages.

Hepp, H. and Offenbartl, H.; "Recycling of Waste Water from Dyehouses After Treatment with Active Alumina"; (vol. 59, No. 7), 1978, pp. 589–592, Germany.

D.B. Erskine and W.G. Schuliger, "Activated Carbon Processes For Liquids"; Chemical Engineering Progress (vol. 67, No. 11), Nov. 1971, USA.

Yasuji Hara, "Adsorption of Anionic Surfactants and Related Compounds from Aqueous Solution onto Activated Carbon and Synthetic Adsorbent"; Journal of Applied Polymer Science (vol. 44) 1992, pp. 1837–1840, USA.

Roberto Leyva–Ramos, "Effect of Temperature and pH on the Adsorption of an Anionic Detergent on Activated Carbon"; Society of Chemical Industry, 1989, Great Britain.

* cited by examiner

*Primary Examiner*—John Hardee
(74) *Attorney, Agent, or Firm*—Snell & Wilmer LLP (57) ABSTRACT

A method for reducing malodors in hydrotropes, such as alkyl aryl sulfonates, is provided that reduces and/or eliminates some or all of the detectable residual odoriferous compounds from hydrotropic compositions using a malodor treatment material, such as, for example, activated carbon. In one aspect of a preferred embodiment of the invention, a malodor treatment material enables the reduction and/or elimination of residual odoriferous compounds from hydrotropic compositions while keeping intact the active hydrotrope solids.

8 Claims, 7 Drawing Sheets

METHOD FOR REDUCING MALODORS IN HYDROTROPIC COMPOSITIONS

CROSS-REFERENCE TO RELATED APPLICATION

This application claims priority from U.S. Provisional Patent Application Ser. No. 60/287,765, entitled "Method for Reducing Malodors in Hydrotropic Compositions," filed May 1, 2001.

FIELD OF INVENTION

This invention generally relates to methods for reducing malodors in hydrotropes, such as alkyl aryl sulfonates, and more particularly, to a method for reducing and/or eliminating some or all of the detectable residual odoriferous compounds from hydrotropic compositions using a malodor treatment material, such as, for example, activated carbon.

BACKGROUND OF THE INVENTION

Activated carbon has been used as a purification agent since Roman times. Carbon treatment is based primarily on a naturally occurring phenomenon called adsorption, wherein molecules of a liquid or gas are trapped by either an internal or external surface of a solid. Activated carbon has a high internal surface area, and is therefore a suitable material for adsorption applications.

Activated carbon can be manufactured from a wide variety of raw materials, and by controlling the creation of the active surface of the carbon particles by carefully selecting and implementing a combination of chemical, mechanical, and thermal processing stages, activated carbon materials designed for specific purification applications are achievable.

Sodium xylene sulfonate is one of a group of compounds known as alkyl aryl sulfonates, and is a commonly used hydrotrope in the consumer products industry. A hydrotrope is a compound that has the ability to enhance the water solubility of other compounds. Some specific examples of hydrotropes include, but are not limited to, sodium cumene sulfonate, ammonium cumene sulfonate, ammonium xylene sulfonate, potassium toluene sulfonate, sodium toluene sulfonate, sodium xylene sulfonate, toluene sulfonic acid, and xylene sulfonic acid. Other useful hydrotropes include sodium polynaphthalene sulfonate, sodium polystyrene sulfonate, sodium methyl naphthalene sulfonate, and disodium succinate.

During the manufacture of hydrotropic compounds, as with most chemical manufacturing processes, it is typical for the final reaction product to comprise not only the desired hydrotropic compound, but also small amounts of unreacted reagents, contaminants, and/or one or more reaction byproducts. In some instances, these unreacted reagents, contaminants, and/or reaction byproducts can be odoriferous, and thus can impart an odor to the final reaction product. For example, residual odoriferous compounds often encountered in connection with the above-listed hydrotropes include xylene, cresol, toluene, cumene, polystyrene, styrene, naphthalene, polynaphthalene, and other compounds. Although such odoriferous compounds typically are present in amounts insufficient to affect the efficacy of the hydrotrope in the end product in which it is used, the odors they impart may be undesirable for some applications. For example, when hydrotropes are employed in consumer product formulations, such as personal care products, it is generally desirable for them not to impart an odor to the resultant formulation, as such an odor may need to be countered with fragrance additives. And indeed, in the formulation of "fragrance-free" products, it is most desirable for the components of the formulations to not impart odors that ultimately must be neutralized in some way.

In the case of the hydrotrope sodium xylene sulfonate, for example, it is common for odoriferous compounds such as xylene and cresol to remain in solution with the sodium xylene sulfonate during manufacture. Although manufacturers and consumers of sodium xylene sulfonate have attempted to reduce and/or eliminate the malodors imparted by these compounds from sodium xylene sulfonate compositions, to date, no effective materials or methods have been identified for this purpose.

Thus, a method is needed to reduce the level of odoriferous compounds in hydrotropic compositions and thus improve the detectable residual odor of such compositions. It is desired to address these issues without increasing the manufacturing costs and/or processing complexity of such hydrotropic compositions and/or the product formulations that utilize these compositions.

SUMMARY OF THE INVENTION

While the way in which the present invention addresses the disadvantages of the prior art will be discussed in greater detail below, in general, the method of the present invention utilizes a suitable malodor treatment material, for example, suitably selected activated carbon, to reduce malodors in hydrotropic compositions.

Novel and contrary to the prior art, the present invention reveals that residual malodors characteristic of some hydrotropic compounds, such as sodium xylene sulfonate, can be reduced and/or eliminated by treating hydrotropic compositions with a material capable of absorbing, adsorbing, binding, trapping, reacting with, or otherwise neutralizing malodor molecules, but which does not deleteriously affect the efficacy of or reduce the amount of the active hydrotrope compounds in the composition. In one aspect of a preferred embodiment of the invention, a malodor treatment material enables the reduction and/or removal of detectable residual odoriferous compounds from hydrotropic compositions while keeping substantially intact the level of active hydrotrope solids in the compositions.

In a further aspect of one embodiment of the present invention, treatment of hydrotropic compositions with a malodor treatment material results in improved color by removing undesirable color bodies from the compositions.

The various aspects and embodiments of the present invention bring about the surprising and unexpected result of achieving the benefits of improved color and residual odor of hydrotropic compositions without substantially reducing the amount of active solids in the composition. In this way, the advantages of the present invention are realized without an appurtenant increase in raw material costs.

Further benefits and advantages of the various aspects and embodiments of the present invention are described in detail hereinbelow.

BRIEF DESCRIPTION OF THE DRAWINGS

The subject matter of the present invention is particularly pointed out and distinctly claimed in the concluding portion of the specification. A more complete understanding of the present invention, however, may best be obtained by referring to the detailed description and claims in connection with the drawing figures, wherein:

DETAILED DESCRIPTION

The following descriptions are of exemplary embodiments of the invention only, and are not intended to limit the scope, applicability or configuration of the invention in any way. Rather, the following description is intended to provide convenient illustrations for implementing various embodiments of the invention. As will become apparent, various changes may be made to various aspects of these exemplary embodiments without departing from the spirit and scope of the invention.

Materials useful in accordance with the present invention generally enable reduction and/or elimination of detectable residual odoriferous compounds characteristic of some hydrotropic compositions, particularly short-chain alkyl aryl sulfonates such as sodium xylene sulfonate, while keeping substantially intact the level of desirable active hydrotrope solids in the composition. Although useful in connection with a variety of hydrotropic compositions, particularly compositions containing short-chain alkyl aryl sulfonates, the present invention will be described herein with regard to an exemplary embodiment for treatment of residual odors in hydrotropic compositions comprising sodium xylene sulfonate or sodium toluene sulfonate.

As used herein, "detectable" generally refers to those odoriferous compounds that are present at levels perceivable through chemical analysis, such as, for example, gas chromatography, and/or that are present at levels perceivable by the human olfactory senses. Moreover, use of a malodor treatment material in accordance with various embodiments of the present invention to reduce and/or eliminate detectable residual odoriferous compounds from hydrotropic compositions may reduce and/or eliminate such compounds by removing them from the hydrotropic composition altogether and/or by physically and/or chemically neutralizing such compounds in the hydrotropic composition, such that such residual odoriferous compounds are relatively undetectable, are present but at lower levels, or not detectable at all when the hydrotropic compositions are utilized alone or in combination with other compounds in a resultant product formulation.

Any material capable of absorbing, adsorbing, binding, trapping, reacting with, or otherwise neutralizing malodor molecules such that the level of detectable residual odoriferous compounds is reduced, but that does not deleteriously affect the efficacy of or substantially decreasing the amount of active hydrotrope compounds in a composition may be used in accordance with the invention. Although not wishing to be bound by any particular theory, in accordance with one aspect of a preferred embodiment of the invention, the malodor treatment material used exhibits a chemical or physical affinity for residual odoriferous compounds in a hydrotropic composition, and preferably does not exhibit a chemical or physical affinity for the active hydrotrope compounds in the composition. Preferably, the malodor treatment material utilized does not impart an odor of its own to the hydrotropic composition. In accordance with one aspect of an exemplary embodiment of the invention, the malodor treatment material exhibits a high rate of adsorption and low resistance to flow with liquids of low to medium viscosity. Moreover, in accordance with another aspect of an exemplary embodiment of the invention, malodor treatment materials that exhibit enhanced adsorption and reactivation characteristics are preferred.

Structurally, malodor treatment materials useful in accordance with various embodiments of the present invention may exhibit characteristics such as, for example, small particle size (i.e., fine mesh), high surface area, specific and/or uniform pore volumes, specific and/or uniform pore size distributions, high density, and/or specific pore shapes or structures. Malodor treatment materials may exhibit any one of these structural characteristics or any combination of these characteristics. Such structural characteristics may enhance the efficiency of various malodor treatment mechanisms, such as, for example, adsorption.

In accordance with one aspect of an exemplary embodiment the present invention, carbonaceous materials are utilized to reduce or eliminate residual odoriferous compounds from hydrotropic compositions, and preferably, activated carbon materials are utilized. Although various properties of activated carbon will be discussed herein, other carbonaceous materials or other malodor treatment materials exhibiting similar properties are likewise useful in accordance with the exemplary embodiment described herein.

In accordance with one aspect of an exemplary embodiment of the invention, wherein the malodor treatment material comprises an activated carbon material, the activated carbon material preferably will exhibit pores smaller than about 100 Angstroms, preferably smaller than about 50 Angstroms, and most preferably smaller than about 20 Angstroms. A uniform pore size distribution is preferable; however, activated carbon materials exhibiting a system of macropores (i.e., pores larger than about 250 Angstroms) permeating throughout particles that otherwise exhibit pore sizes on the order of those recited above may also be advantageous. Iodine and molasses numbers measure pore size distribution. Iodine number is a relative measure of pores at sizes from about 10 to about 20 Angstroms. It is reported in milligrams of elemental iodine adsorbed per gram of activated carbon. Molasses number measures pores larger than about 28 Angstroms. In accordance with one aspect of an exemplary embodiment of the invention, the activated carbon material preferably will exhibit an iodine number of at least about 600 mg/g, more preferably will exhibit an iodine number of at least about 900 mg/g, and most preferably will exhibit an iodine number of at least about 1000 mg/g. In accordance with another aspect of an exemplary embodiment of the invention, the activated carbon material preferably will exhibit a molasses number of from about 200 to about 300 mg/g, more preferably will exhibit a molasses number of from about 220 to about 250 mg/g, and most preferably will exhibit a molasses number of from about 230 to about 235 mg/g.

Preferably, activated carbon materials will have a particle size of no greater than about 8×30 mesh, more preferably no greater than about 12×40 mesh, and even more preferably no greater than about 20×50 mesh. Preferably, the activated carbon material will exhibit a mean particle diameter of from about 0.2 to about 1.7 millimeters (mm), more preferably from about 0.5 to about 1.5 mm, and most preferably from about 0.9 to about 1.1 mm. Abrasion numbers represent the relative degree of particle size reduction act after tumbling with a harder material. No reduction is rated 100, while complete pulverization of the material is rated 0. In accordance with another aspect of an exemplary embodiment of the invention, the activated carbon material preferably will exhibit an abrasion number of from about 60 to about 97, more preferably will exhibit an abrasion number of from about 75 to about 95, and most preferably will exhibit an abrasion number of from about 80 to about 90.

Activated carbon materials manufactured from bituminous coal are likely to demonstrate one or more of the above-described structural characteristics, although activated carbon materials having similar characteristics may be manufactured from a variety of raw materials, including, for example, wood, peat, coconut shells, petroleum coke, and other materials exhibiting high carbon content. Activated carbon materials activated by high temperature steam processing, and characteristically exhibiting a high surface area, large pore volume, and a uniform pore structure, are used advantageously in accordance with one aspect of a preferred embodiment of the invention. In another aspect of an exemplary embodiment of the invention, the activated carbon material can be reactivated for repeated use, such as by thermal processing.

One example of an activated carbon material exhibiting one or more of the above-described structural characteristics useful in accordance with a preferred embodiment of the present invention is that sold under the trademark CAL™, by Calgon Carbon Corporation of Pittsburgh, Pa. CAL™ brand activated carbon generally exhibits physical characteristics, e.g., small pore size, relatively low pore size distribution, fine mesh, and others, along the lines set forth hereinabove. In addition, the material exhibits a high abrasion number. Abrasion numbers represent the relative degree of particle size reduction after tumbling with a harder material. No reduction is rated 100, while complete pulverization of the material is rated 0. In accordance with another aspect of an exemplary embodiment of the invention, the activated carbon material preferably will exhibit an abrasion number of from about 60 to about 97, more preferably will exhibit an abrasion number of from about 75 to about 95, and most preferably will exhibit an abrasion number of from about 80 to about 90.

In accordance with one aspect of a preferred embodiment of the present invention, activated carbon is added to a hydrotropic composition, for example, a sodium xylene sulfonate solution, in an amount of from about 0.10 to about 5.0 grams per 100 milliliters of solution, preferably from about 0.25 to about 1.0 grams per 100 milliliters of solution, and most preferably about 0.50 grams per 100 milliliters of solution. As the concentration of activated carbon in the solution increases beyond the preferred range, the raw material and processing costs of the sodium xylene sulfonate solution may increase without commensurate benefit in residual odor reduction.

As an added advantage, at least in some applications, a hydrotropic composition treated in accordance with various aspects of the present invention may undergo a color change through treatment with a suitable malodor treatment material. For example, while an untreated sodium xylene sulfonate solution may exhibit a translucent pale yellow or light straw color, when treated with a suitable amount of activated carbon in accordance with the above description, a sodium xylene sulfonate solution may become nearly colorless, or water-white, or sometimes even exhibiting a slight bluish cast. It is therefore evident that in addition to reducing the levels of residual odoriferous compounds in the sodium xylene sulfonate solution, the activated carbon treatment may also serve to improve the color of hydrotropic compositions by removing color bodies from the compositions.

In yet a further aspect of an exemplary embodiment of the present invention, it is observed that treatment of sodium xylene sulfonate with a malodor treatment material, such as, for example, activated carbon, does not adversely affect the composition of hydrotrope in solution. That is, although the malodor treatment material effectively removes and/or eliminates detectable odoriferous compounds and/or color bodies from the hydrotropic composition, it does not capture a significant amount of the active hydrotrope solids in the composition. Stated another way, suitable malodor treatment materials in accordance with various aspects of the present invention are capable of decreasing a sufficient amount of the residual odoriferous compounds in a hydrotropic composition without substantially decreasing the amount of the active hydrotrope solids in the composition. Preferably, treatment with a suitable malodor treatment material results in less than about 2% reduction by weight of active hydrotrope solids in the hydrotropic composition, and more preferably results in less than about 1% reduction by weight of active hydrotrope solids in the composition. Optimally, and as may be the case in many applications, insignificant active solids are removed or otherwise inhibited through treatment with a suitable malodor treatment material, and thus, most preferably suitable treatment results in less than about 0.5% reduction by weight of active hydrotrope solids in the composition.

The step of contacting the malodor treatment material, such as, for example, activated carbon, with the hydrotropic composition to be treated may be effectuated in any vessel suitable to contain the malodor treatment material and composition, and to ensure prolonged intimate contact between the two during treatment. If, for example, a composition is to be treated in a batch-wise process with a malodor treatment material comprising an activated carbon material, an open tank or other vessel equipped with means for agitating the mixture of activated carbon and the hydrotropic composition may be suitable to achieve these objectives. On the other hand, if, for example, a composition is to be treated in a continuous operation, a column or other closed vessel may be utilized that contains a fixed activated carbon bed, through which the composition may be passed to achieve prolonged intimate contact between the activated carbon and the hydrotropic composition to be treated. Although a wide variety of batch and continuous processing schemes are possible that will achieve the purposes of the present invention, one exemplary continuous processing scheme employs one or more fixed activated carbon bed columns, approximately four (4) feet wide and approximately eight (8) feet tall, into the top of which the hydrotropic composition to be treated is introduced. The hydrotropic composition percolates through the fixed activated carbon bed(s) and the treated solution is discharged from the bottom of the column. After discharge of the treated composition from the column, the activated carbon within the column may be reactivated by conventional process techniques and reused in another operation. In another aspect of a preferred embodiment of the invention, hydrotropic compositions are treated with activated carbon at ambient temperature.

Examples 1 and 2 set forth hereinbelow demonstrate the effectiveness of the present invention in reducing residual malodors in hydrotropic compositions, such as, for example, sodium xylene sulfonate and sodium toluene sulfonate.

EXAMPLE 1

A mixture of 5 weight percent CAL™ brand activated carbon (Type PWA-C Pulverized) from Calgon Carbon Corporation (10.53 grams), and 95 weight percent sodium xylene sulfonate (40.0% active solids) from Rutgers Organics Corporation in Harrison, Ohio, Lot 99-028-4LS Untreated (200.0 grams), was blended in a beaker and continuously stirred for approximately two hours at ambient temperature. The mixture was then filtered to separate the solid activated carbon from the sodium xylene sulfonate. The color of the resulting sodium xylene sulfonate composition was "water white," with a slight bluish cast (as opposed to the light straw color of the untreated sodium xylene sulfonate composition). Subjected to human odor evaluation, the treated sodium xylene sulfonate composition exhibited no detectable residual malodor.

EXAMPLE 2

A mixture of 0.5 grams CAL™ brand activated carbon (Type PWA-C Pulverized) from Calgon Carbon Corporation and 100 mL sodium toluene sulfonate (40.0% active solids) from Rutgers Organics Corporation in Harrison, Ohio, Lot S0009-1164-4ST (trademark Naxonate® 4ST) was blended in a beaker and continuously stirred for approximately forty-five (45) minutes at ambient temperature. The mixture was then filtered to separate the solid activated carbon from the sodium toluene sulfonate. The color of the resulting sodium toluene sulfonate was "water white." Subjected to human odor evaluation, the treated sodium toluene sulfonate exhibited no detectable residual malodor.

EXAMPLE 3

In this Example, various samples of sodium xylene sulfonate (represented by SXS in Table 1) were prepared, and the samples were treated with activated carbon at various concentration levels (as set forth below in Table 1). Each of the samples treated contained 100.0 milliliters of sodium xylene sulfonate (40.0% active solids) from Rutgers Organics Corporation in Harrison, Ohio, Lot 99-028-4LS, and CAL™ brand activated carbon (Type PWA-C Pulverized) from Calgon Carbon in the amounts designated below.

TABLE 1

| Sample | SXS (ml) | Activated Carbon (g) |
| --- | --- | --- |
| Control | 100 | — |
| B | 100 | 0.01 |
| C | 100 | 0.025 |
| D | 100 | 0.05 |
| E | 100 | 0.1 |
| F | 100 | 0.25 |
| G | 100 | 0.5 |
| H | 100 | 1.0 |
| I | 100 | 5.0 |

For each sample, the sodium xylene sulfonate and activated carbon were blended in a beaker and the mixture was continuously stirred for approximately two hours at ambient temperature. The samples were then filtered to separate the solid activated carbon from the treated sodium xylene sulfonate samples, and each of the treated sodium xylene sulfonate samples was subjected to analysis by solid phase microextraction (SPME) (sometimes referred to in the art as "head space chromatography").

The effectiveness of the aforesaid treatment in reducing the concentration of aromatic xylene molecules in each of the treated samples is demonstrated by the chromatograms in FIGS. 1a–1i. The peaks at the far left side of each chromatogram (T=4.00–6.00; x-axis) are indicative of aromatic xylene compounds in the samples, and a higher peak indicates a higher level of xylene compounds in a particular sample. It should be noted that the chromatographic analyses for the aromatic xylene compounds were completed over the course of two days. The Control sample (i.e., no carbon treatment) and Sample I (5.0 g carbon/100 ml sodium xylene sulfonate) were analyzed the same day, and the resultant chromatograms have a y-axis Abundance scale of approximately 25,000 units maximum. Sodium xylene sulfonate samples treated with intermediate levels of activated carbon were then analyzed, and the results of these analyses were reflected in the chromatograms of FIGS. 1b–1h. As one skilled in the art is aware, the response factor for a chromatograph may vary—and generally does vary—from day to day. In this case, the Abundance scale (y-axis) on the respective chromatograms for Samples B–H shows a maximum slightly in excess of 120,000 units, which differs from the Abundance scale for the chromatograms for the Control and Samples I (i.e., about 25,000 units maximum) that were generated on a different day.

Figure 1A:
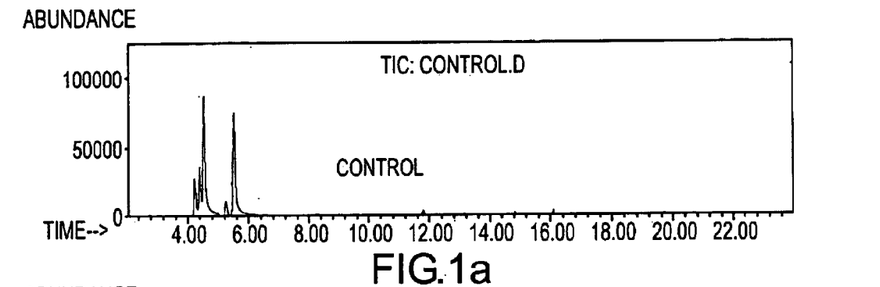
FIGS. 1a–1j comprise chromatograms for an air blank and various hydrotropic composition samples treated with various levels of an activated carbon material in accordance with a preferred embodiment of the present invention.
Figure 1B:
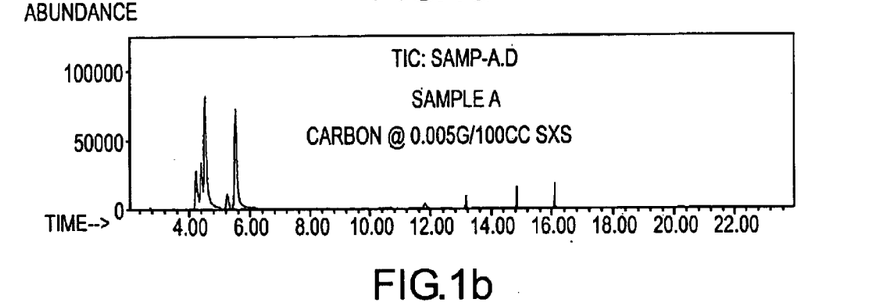
Figure 1C:
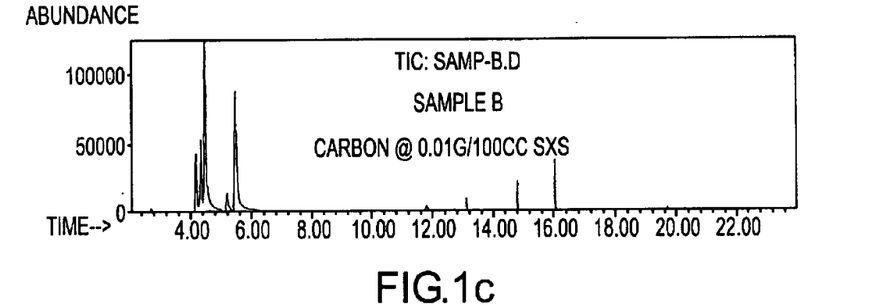
Figure 1D:
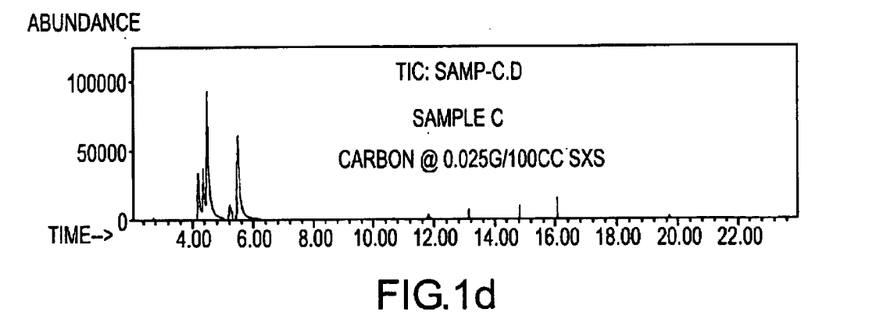
Figure 1E:
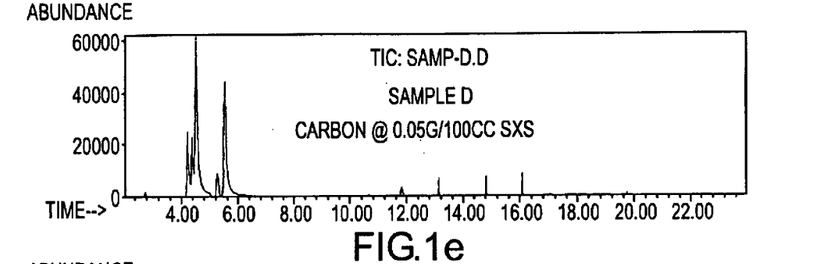
Figure 1F:
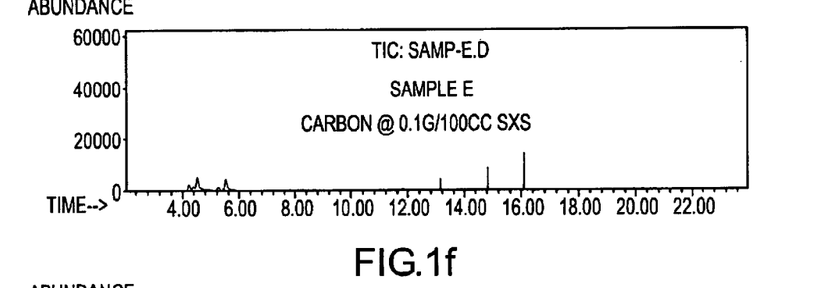
Figure 1G:
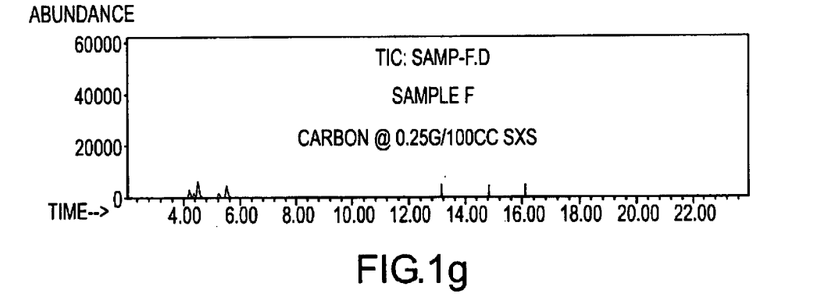
Figure 1H:
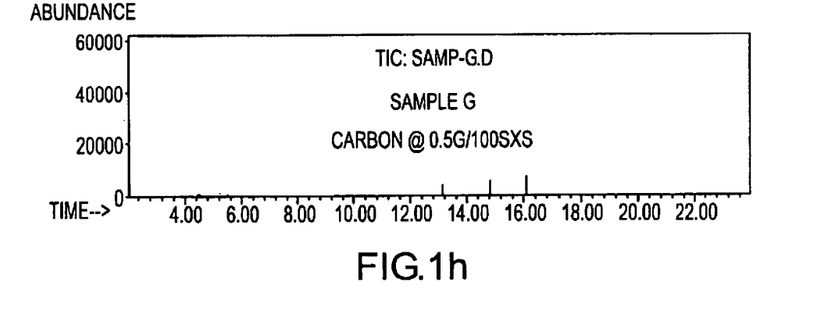
Figure 1I:
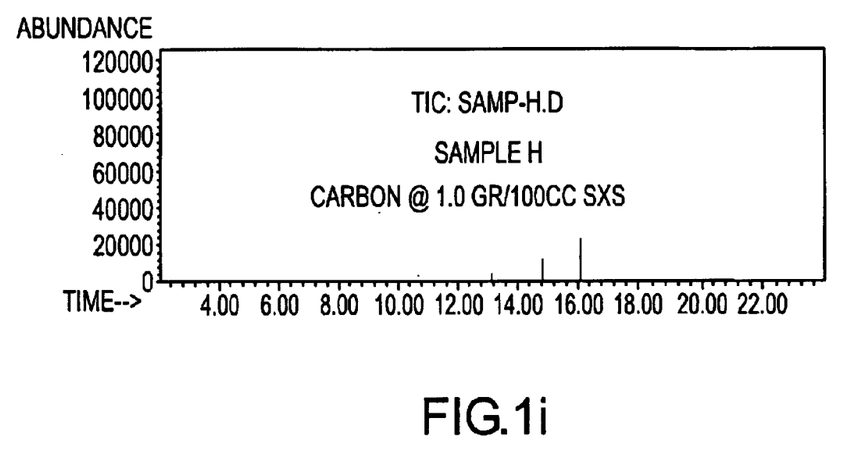
Figure 1J:
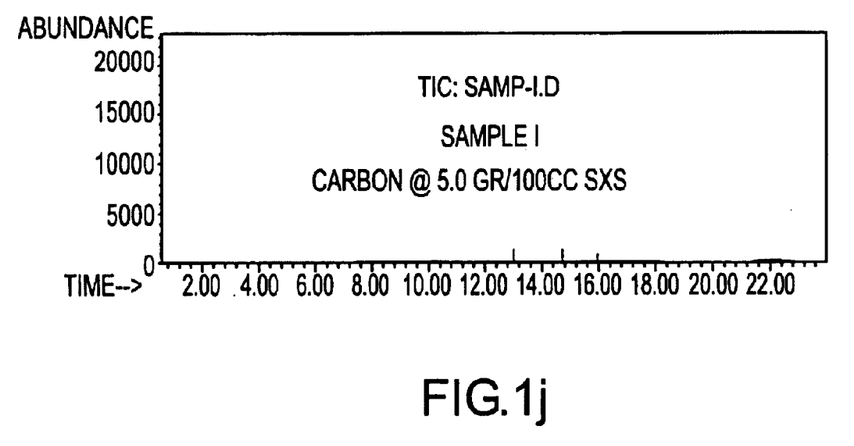

The chromatogram of FIG. 1a reflects the analysis of a Control sample of untreated sodium xylene sulfonate. The highest peak between T=4.00 and T=6.00 reaches an Abundance (y-axis) level of approximately 24,000 units. The chromatograms of FIGS. 1b–1i reflect analyses of Samples B–I, sodium xylene sulfonate samples treated with progressively greater amounts of activated carbon, as indicated in Table 1. The highest peak between T=4.00 and T=6.00 for Sample B indicates an Abundance (y-axis) level of approximately 120,000 units, whereas progressively lower peak Abundance levels are reflected for Samples C–E. No peaks at all appear in the chromatograms for Samples G–I. Thus, it is apparent from these chemical analyses that a substantial amount of the residual xylene compounds in a sodium xylene sulfonate solution is adsorbed by activated carbon at a concentration level of approximately 0.1 grams of activated carbon per 100 milliliters of sodium xylene sulfonate, and substantially all of the residual xylene compounds are adsorbed by activated carbon at concentration levels equal to or greater than approximately 0.5 grams of activated carbon per 100 milliliters of sodium xylene sulfonate.

EXAMPLE 4

In this Example, Samples E, F, G and I from Example 3, as well as an air "blank" (i.e., headspace only, no sodium xylene sulfonate) were further analyzed to determine the levels of residual cresol compounds in the samples. On the chromatograms in FIGS. 2a–2e, residual cresols are indicated by a peak at or about T=14.00–14.20 on the x-axis.

Figure 2A:
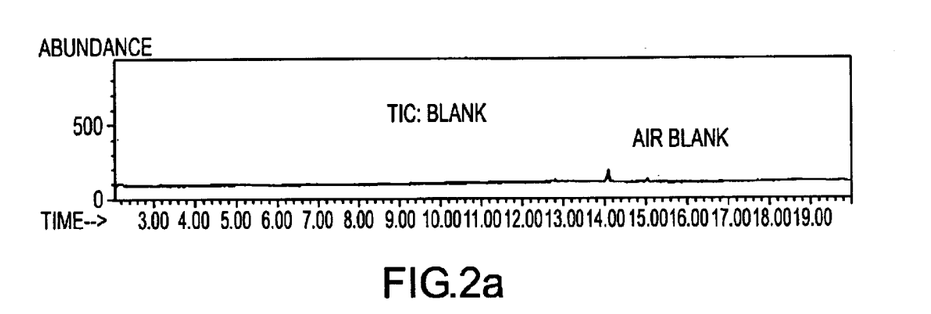
FIGS. 2a–2e comprise a series of chromatograms that further demonstrate the various surprising and novel aspects of the present invention.
Figure 2B:
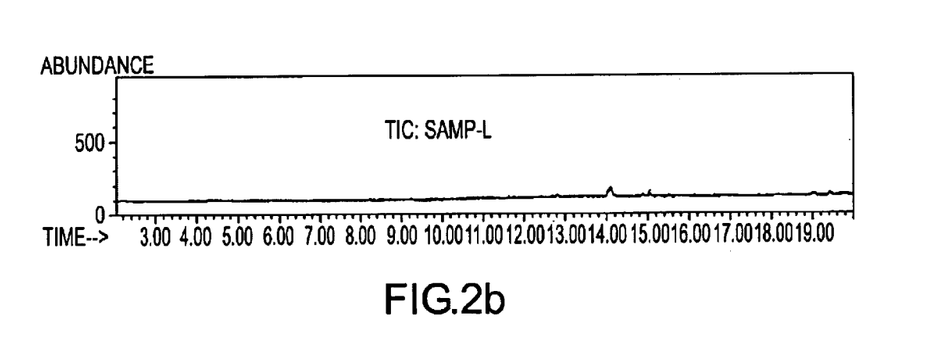
Figure 2C:
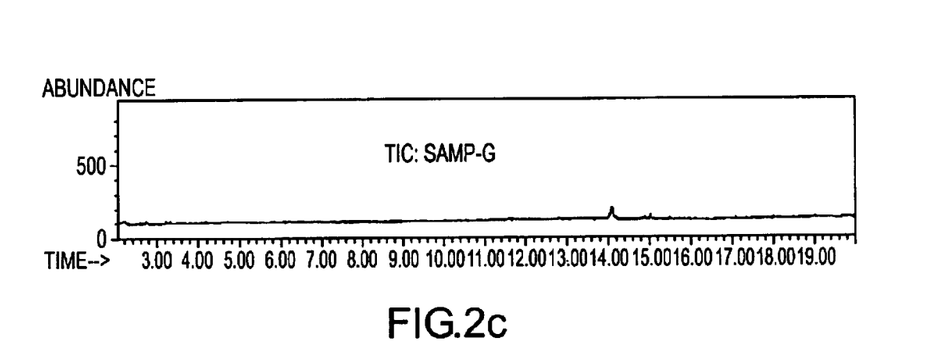
Figure 2D:
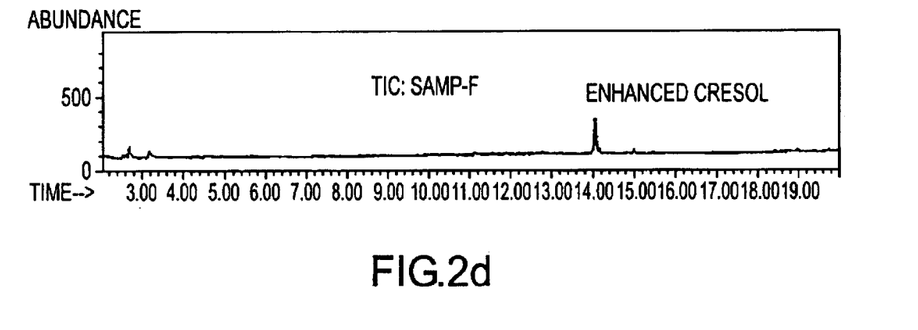
Figure 2E:
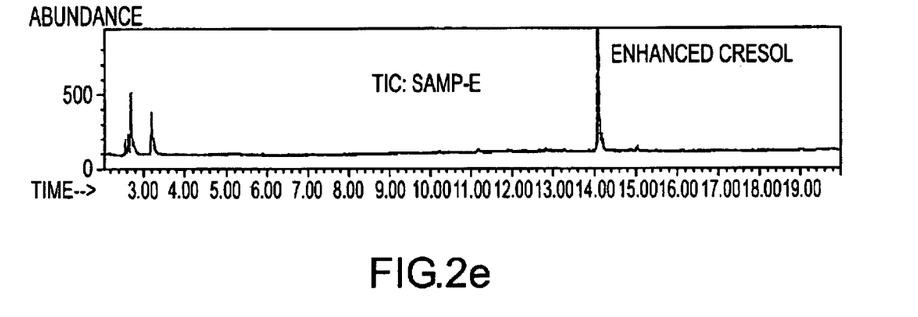

The effectiveness of the aforesaid treatment in reducing the concentration of odoriferous cresol molecules in Samples E, F, G, and I is clearly demonstrated by the chromatograms in FIGS. 2a–2e. In FIG. 2e, the chromatographic analysis of Sample E indicates an Abundance level (y-axis) of about 1000 units for residual cresol compounds. Sample F, treated with a higher level of activated carbon than Sample E, shows an improvement in residual cresol level over Sample E in that the peak at T=14.00 reaches an Abundance level of only about 300 units (FIG. 2d). Samples G and I (FIGS. 2c and 2b, respectively) show residual cresol levels eliminated, since the peaks shown are simply the air blank (FIG. 2a), indicating a substantial reduction in the levels of such compounds in the sodium xylene sulfonate composition by treatment with activated carbon at a concentration level of at least about 0.5 grams of activated carbon per 100 milliliters of sodium xylene sulfonate.

EXAMPLE 5

In this Example, samples of sodium xylene sulfonate compositions treated with activated carbon at concentration levels of approximately 0.5 grams of activated carbon per 100 milliliters of sodium xylene sulfonate were prepared and subjected to SPME, as described above. A series of chromatograms reflecting the results of these analyses appears in FIGS. 3a–3e.

Figure 3A:
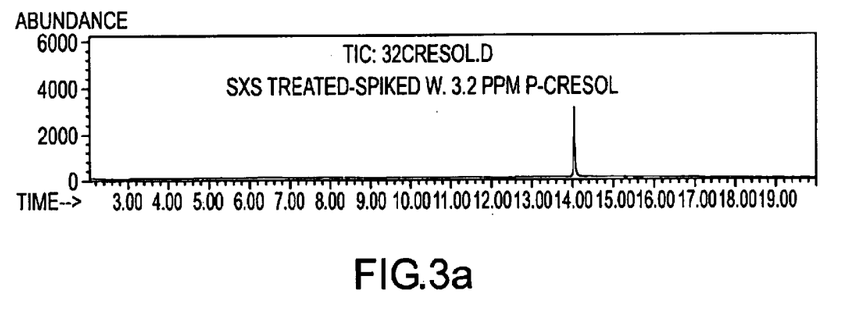
FIGS. 3a–3e comprise chromatograms for an untreated hydrotropic composition sample and nine hydrotropic composition samples treated with various levels of an activated carbon material in accordance with one preferred embodiment of the present invention.
Figure 3B:
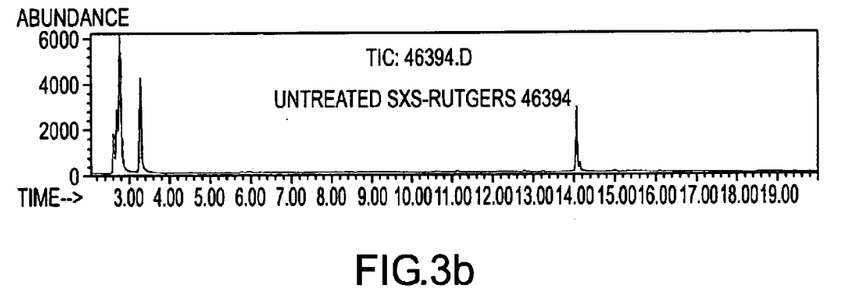
Figure 3C:
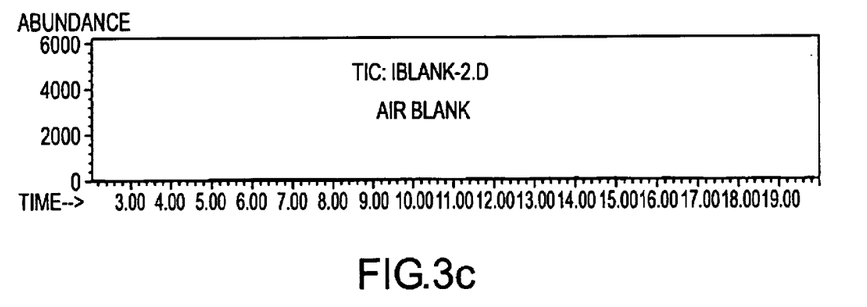
Figure 3D:
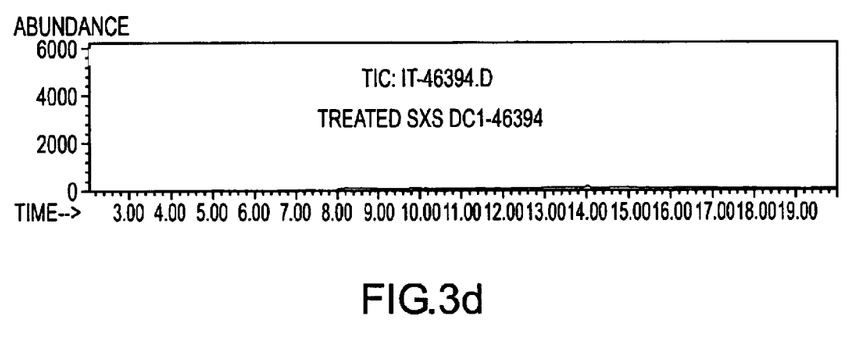
Figure 3E:
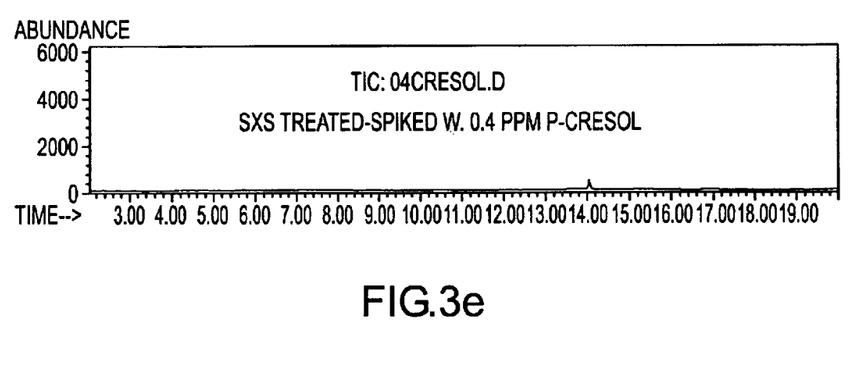

FIGS. 3a and 3e reflect the analyses of two samples of treated sodium xylene sulfonate composition, into which small amounts of cresol compounds were added (3.2 PPM and 0.4 PPM, respectively). These chromatograms are useful in comparing the cresol concentrations of treated and untreated sodium xylene sulfonate samples to known cresol concentrations, for the purpose of quantification.

FIG. 3b is a chromatogram reflecting the residual xylene and cresol concentrations in an untreated sodium xylene sulfonate sample.

FIG. 3c is a chromatogram of an air "blank," similar to that utilized in Example 3. No xylene or cresol peaks appear on the chromatogram in FIG. 3c, indicating an absence of such compounds.

FIG. 3d is a chromatogram reflecting the residual xylene and cresol concentrations in a treated sodium xylene sulfonate sample composition. The chromatogram in FIG. 3d closely approximates the chromatogram for the air "blank" in FIG. 3c, and indicates a substantial absence of xylene and cresol compounds in the treated sample.

EXAMPLE 6

Sodium xylene sulfonate is typically commercially available as mixture of active solids in water. Two samples of activated carbon-treated sodium xylene sulfonate were analyzed to estimate the amount of active solids lost as a result of activated carbon treatment. The samples before treatment comprised about 40.0 to about 42.0% minimum active solids (by weight). Each treated sample was weighed, placed in an open vessel, and heated for 24 hours at 100° C. to remove the water from the sample composition. The residual material in the vessel, comprising the sodium xylene sulfonate active solids, was weighed and compared to the solids content of the untreated sodium xylene sulfonate.

| Sample A: | Original weight of SXS solution sample: | 82.25 grams |
| | Weight of residual solids after heating: | 34.42 grams |

$$\frac{34.42}{82.25} \times 100 = 41.85\% \text{ solids}$$

| Sample B: | Original weight of SXS solution sample: | 82.30 grams |
| | Weight of residual solids after heating: | 34.20 grams |

$$\frac{34.20}{82.30} \times 100 = 41.55\% \text{ solids}$$

Thus, it is evident that treatment of sodium xylene sulfonate with activated carbon in accordance with the above detailed description has a negligible effect on the amount of active solids in the solution. Indeed, this Example demonstrates the effectiveness of decreasing the detectable amount of residual odoriferous compound in a hydrotropic composition without substantially decreasing the amount of the hydrotrope in the hydrotropic composition.

Hydrotropic compositions treated in accordance with the present invention may beneficially be utilized in a variety of applications, and in particular, consumer product formulations. As discussed hereinabove, when hydrotropic compositions are used in consumer product formulations, such as, for example, personal care products and/or cosmetic products, it may be desirable for the hydrotropic compositions not to impart an odor to the resultant product. Examples of consumer product formulations in which hydrotropic compositions treated in accordance with the present invention may be useful may be found, for instance, in U.S. Pat. No. 6,204,230, entitled "Antibacterial Compositions Containing a Solvent, Hydrotrope, and Surfactant," issued Mar. 20, 2001 to Taylor et al., and U.S. Pat. No. 6,107,261, entitled "Compositions Containing a High Percent Saturation Concentration of Antibacterial Agent," issued Aug. 22, 2000 to Taylor et al., both of which are incorporated by reference herein. For example, an antibacterial composition comprising a polyhydric solvent, a surfactant, an antibacterial agent, and a hydrotrope, wherein the hydrotrope comprises a hydrotropic composition treated in accordance with various aspects of the present invention, and wherein the antibacterial composition does not exhibit detectable malodors, may be manufactured in accordance with the formulations and methods disclosed in U.S. Pat. Nos. 6,204,230 and 6,107,261 and disclosed herein. In general, however, any composition that would otherwise comprise an untreated hydrotropic composition may beneficially utilize a hydrotropic composition treated in accordance with the present invention.

Various principles of the invention have been described in illustrative embodiments. However, many combinations and modifications of the above-described structures, arrangements, proportions, elements, materials and components, used in the practice of the invention, in addition to those not specifically described, may be varied and particularly adapted to specific environments and operating requirements without departing from those principles. Stated another way, the above description presents exemplary modes contemplated in carrying out the invention and the techniques described are susceptible to modifications and alternate constructions from the embodiments shown above. Other variations and modifications of the present invention will be apparent to those of ordinary skill in the art, and it is the intent of the appended claims that such variations and modifications be covered. In addition the order of the described steps is not necessarily material, unless otherwise noted. Furthermore, various steps can be altered, added, or deleted to the embodiments described and illustrated in the application without a deleterious effect on the present invention.

Consequently, it is not the intention to limit the invention to the particular embodiments disclosed. On the contrary, the invention is intended to cover all modifications and alternate constructions falling within the scope of the invention, as expressed in the following claims when read in light of the description and drawing figures. No element described in this specification is necessary for the practice of the invention unless expressly described herein as "essential" or "required."

What is claimed is:

1. A method for reducing the detectable level of odoriferous compounds in hydrotropic compositions comprising:
   providing a hydrotropic composition comprising a hydrotrope and a detectable amount of an odoriferous compound; and,
   contacting at least a portion of said hydrotropic composition with activated carbon in a fixed bed column, wherein contact with said activated carbon decreases the detectable level of said odoriferous compound in said hydrotropic composition without substantially decreasing the amount of said hydrotrope in said hydrotropic composition.

2. The method of claim 1 wherein said step of providing a hydrotropic composition comprises providing a hydrotropic composition comprising an alkyl aryl sulfonate.

3. The method of claim 1 wherein said step of providing a hydrotropic composition comprises providing sodium cumene sulfonate, ammonium cumene sulfonate, ammonium xylene sulfonate, potassium toluene sulfonate, sodium toluene sulfonate, or sodium xylene sulfonate.

4. The method of claim 1 wherein said step of providing a hydrotropic composition comprises providing toluene sulfonic acid, xylene sulfonic acid, sodium polynaphthalene sulfonate, sodium polystyrene sulfonate, sodium methyl naphthalene sulfonate, or disodium succinate.

5. The method of claim 1 wherein said step of providing a hydrotropic composition comprises providing a hydrotropic composition wherein said odoriferous compound comprises xylene.

6. The method of claim 1 wherein said step of providing a hydrotropic composition comprises providing a hydrotropic composition wherein said odoriferous compound comprises cresol.

7. The method of claim 1 wherein said step of providing a hydrotropic composition comprises providing a hydrotropic composition wherein said odoriferous compound comprises toluene.

8. The method of claim 1 wherein said step of providing a hydrotropic composition comprises providing a hydrotropic composition wherein said odoriferous compound comprises cumene, styrene, naphthalene, polynaphthalene, and/or polystyrene.

* * * * *